United States Patent [19]

Jones

[11] Patent Number: 4,867,142

[45] Date of Patent: Sep. 19, 1989

[54] SELF ACTUATED LOMBAR TRACTION APPARATUS

[75] Inventor: J. Paul Jones, Chester Springs, Pa.

[73] Assignee: PRD Corporation, Exton, Pa.

[21] Appl. No.: 155,476

[22] Filed: Feb. 12, 1988

[51] Int. Cl.[4] .......... A61F 5/00

[52] U.S. Cl. .......... 128/57; 128/75; 272/145; 272/144

[58] Field of Search .......... 128/24 R, 24.2, 24.3, 128/44, 57, 58, 56, 60, 61, 62 R, 69, 75, 78; 272/116, 126, 125, 128, 134, 143, 144, 145, 903, 136, 137, 138; 297/452

[56] References Cited

U.S. PATENT DOCUMENTS

| | | | |
|---|---|---|---|
| 2,219,624 | 10/1940 | Dixon | 128/57 |
| 2,623,518 | 12/1952 | Vaquette | 128/75 |
| 3,271,028 | 9/1966 | Albin | 272/144 |
| 3,378,259 | 4/1968 | Kupchinski | 272/144 |
| 4,292,962 | 10/1981 | Krause | 272/145 |
| 4,739,749 | 4/1988 | Lindley | 128/75 |

FOREIGN PATENT DOCUMENTS

| | | | |
|---|---|---|---|
| 2160642 | 6/1973 | Fed. Rep. of Germany | 272/145 |

*Primary Examiner*—Edgar S. Burr
*Assistant Examiner*—Kimberly L. Asher

[57] ABSTRACT

This invention is in the general field of Rehabilitation Apparatus for the human back and, in particular, it provides a self-help, portable apparatus, which allows the operator to apply intermittant traction to the lower Lombar region of his back. The position of a radius surface in relation to the position of the operators knees, places the Lombar area of his back on an outside circle that is at the peak of the radius surface. The traction force that is created by the weight of the upper Torso of the operator may be lessened by the use of the operators arms, or it may be increased by pulling on an Adjustable Pull Bar.

The apparatus may also be used for strengthening exercises for the back muscles, while the spinal column remains under decompression. The invention is designed for quick assembly, and equally quick "knock down" for storage or transporting.

5 Claims, 3 Drawing Sheets

SELF ACTUATED LOMBAR TRACTION APPARATUS

BACKGROUND

Back problems and associated ailments constitute one of the largest segments of medical expenses in the country. The field of back treatment, surgery, and the analgesic medicines prescribed for same, are almost as much as all other fields combined. It has been estimated at the time of this writing that over Forty Billion dollars are lost each year in Industry alone, because of dehabilitating back problems.

Most of the prominent and successful Osteopathis Physicians who deal with human spinal column problems admit that over 75 percent of the cases can be stabilized and/or cured by exercises that bring toning to the ligaments and muscles that support the Spinal Column.

Any minor injury to the back, from falls etc., usually causes some injury or even tearing of the ligaments of the vertebrae which make up the spinal column. During the period of repair, and unless the person is completely immobilized, the body muscle system tenses up to support the back in the manner of guy wires that are set up to support a weakened tree. Since the muscle system itself is designed to be used dynamically, it does not function well when in constant tension; and especially when not in good muscle tone. In a typical overweight and sedentary person, this fact results in fatiguing of the muscle system; and even severe spasms, which constitute over 75% of the symptoms that are being treated by the physicians.

The usual treatment from a non specializing physician is, "rest and analgesic pills to cut the Pain". The average person cannot give up work to carry out this simple prescription and, as a result, gets into a vicious circle of degenerating back condition. Adequate exercise, if it is possible with a worsening condition, can help the muscle system do its "temporary" job of sustaining the spinal column; however, this does not reach the seat of the basic problem, which often requires ligament repair. Ligament repair, in turn, requires a decompressive exercise rather than the usual compressive types; and it is advantageous to use prescribed intermittant traction to avoid making the protective muscles tense up, or even go into spasm.

It is an unfortunate fact, that all exercising machines, such as those used in body building spas, etc.,—and even the body toning exercises without machines—are all compressive to the spinal column. The effect of compression on the Spinal Column is usually the most critical in the lower Lombar region of the back.

There have been successful machines , for the last fifty years, which apply cyclic traction to the lower back, while the patient is laying in the prone position. The machinery requires a large table in addition to the cycling mechanism; and these machines require a large amount of space (i.e. usually a whole small antiroom); and they also require an attendant to strap in the patient, and to monitor the action of the machine.

Treatment with this type of intermittant traction machine has produced near one hundred percent results in the eighty percent segment of ailing backs that are directly attributed to the degeneration of the ligaments and the muscle systems. The need for costly space, and the need for an attendant that is not being continuously used, has made the present machines "non productive" for the private osteopathic physician.

To quote the average osteopathic physician, "It usually requires up to ten consecutive visits to cure the typical back condition; however, the pain can be substantially reduced to an acceptable level in as few as three visits. This usually results in the patient not continuing for the total needed visits."

The typical degenerative back condition requires both immediate attention, and continuing attention on a long term basis. Many of the physicians agree that most of these patients would need a self-operated apparatus which should be inexpensive and "durable for life"; and should be in the category of the typical exercise apparatus. The operator should also be in complete control of the exertion and the pressure that is applied in the treatment, which would not require and attendant, and, thereby, not be a potential liability to the Physician.

It is, therefore, one object of this invention to provide a simple "knockdown" apparatus, which may be used by an individual to administer self-help, in the rehabilitation of common Lower Back (Lombar area) problems.

It is another object of this invention to provide a durable and easily assembled apparatus which will, after quick and easy assembly, allow a person to apply intermittant traction (Pull) to the Lombar section of the Spinal Column; for the purpose of aligning the vertebrae, and strengthening the connective ligaments and associated supporting muscles, with non-compressive exercise.

It is still another object of this invention to provide an apparatus that will enable a person, with a typical lower back problem, to correct a mis-allignment of the vertebrae quickly; before necessarily going to a physician. It is universally acknowledged that mis-allignments should be corrected as soon as possible; and preferably before going to bed for a single night.

It is yet another object of this invention to provide, without any conversions, a self activated method for (1) aligning the Spinal Column in the Lombar area, (2) Providing Intermittant Traction to the connecting ligaments of the Spinal Column, and (3) Enabling the Operator to carry out strengthening exercise for his supporting back muscles; under non-compressive conditions.

OPERATIONAL DESCRIPTION

It is of utmost importance, because of liability and corressponding high medical insurance for the physicians, that any apparatus that is designed for prescribed self-help, be free of things that are not entirely under control of the Operator-Patient.

This invention provides a unique means for both applying controlled intermittant traction (decompression) to the Spinal Column of an operator; and, in addition, provides a means of doing back strengthening exercises, while still maintaining a decompressive bias on the the Spinal Column.

A basic requirement for portability in relatively large apparatus is ease of assembly and disassembly. Both Lightness and long term durability are also essential requisites for truly portable equipment.

With reference to the apparatus drawings in FIGS. 1 thru 4, the parts that are used by the Operator will be described in the sequence of usage. There is a Kneeling Pad 5 on the Kneeling Panel 3 to make it more comfortable to the Operator 10. As soon as the Operator has kneeled on the pad he may lean over the Radius Surface Cover 8 to test his reach to the Cross Rod 2A, which is mounted in the Adjustment Holes 2B. Should the Cross Rod 2A need adjustment to the reach of the Operator 10, it may be removed by unscrewing the Knob Bolts 4A and reinserting them into the correct Grip Rod Mounting Holes 2B, before retightening them into the Cross Rod 2A ends.

Figure 3:
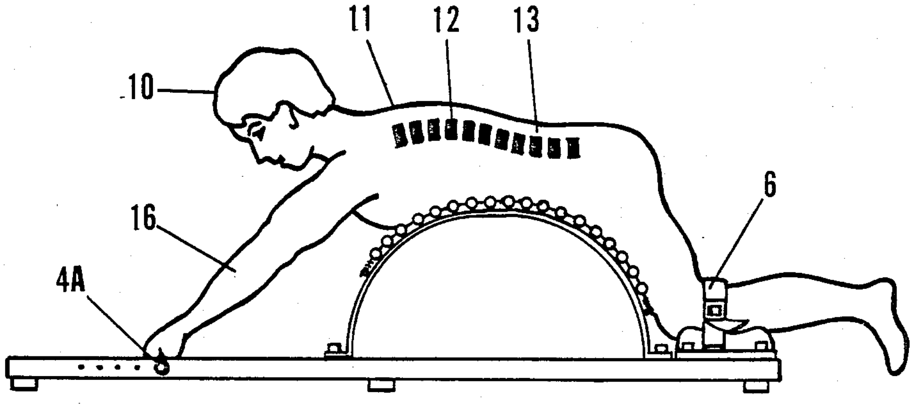
FIG. 3 shows a side view of the apparatus with an operator in "starting position"; with the lower legs buckled to a kneeling pad; the center torso over the Tubular cover on the Radius Supports; and the forearms grasping the adjustable Front Crossbar. The representation of the Spinal Column is shown in a neutral non-extended condition.

In the starting position, shown in FIG. 3, the Operator 10 is comfortable; after tightening the Leg Retaining Belts 6A,6B over the back of the legs, with the Back 11 in a horizontal position, and with no traction force on the Spinal Column 12. As soon as the Operator relaxes his Arms 16 slowly, as shown in FIG. 4, his upper torso, head, and arms will drape over the Radius Cover 8, which is supported by the Radius Members 7A,7B; and a Traction Force 14 will be created along the topside of the Operators Back 11, and through the Spinal Column 12, in the Lombar Area 13; by the pull of gravity on the upper torso of the operator and the pull of the operators arms 16.

By using the arms to gently lower the upper torso, a minimum amount of Traction (stretching) force may be applied to the Lower Back Lombar Area 13. If more peak traction is desired by the Operator 10 he may use his Arms 16 to pull on the Cross Bar 2A with a force from zero to 100 pounds and more. The results of this pull will be the effective lengthening of the body, starting at the knees, and reaching peak traction in the Lombar area of the back. There is a resultant separating force along the length of the Spinal Column; and predominantly on the ligaments that are connected to the spinal vertebrae, which are designed to maintain the spinal column in an erect but flexible condition.

Figure 4:
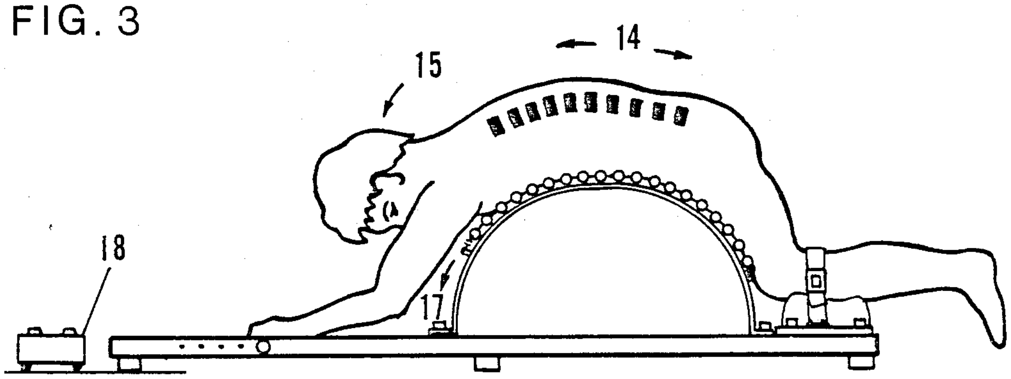
FIG. 4 shows the same side view as above, with traction being applied to the Spinal Column by a combination of (1) the weight of the upper torso and (2) a pulling force from the arms of the Operator. Also shown in the Figure is a "Beep Box", which is preset by the Operator to a desired cycle time and traction "hold" period; and which gives audible "beep" commands to the Operator.

The Operator 10 may repeat the cycle between the position taken in FIG. 4—with a prescribed "dwell time" for holding the pulling position shown in FIG. 4.

Figure 1:
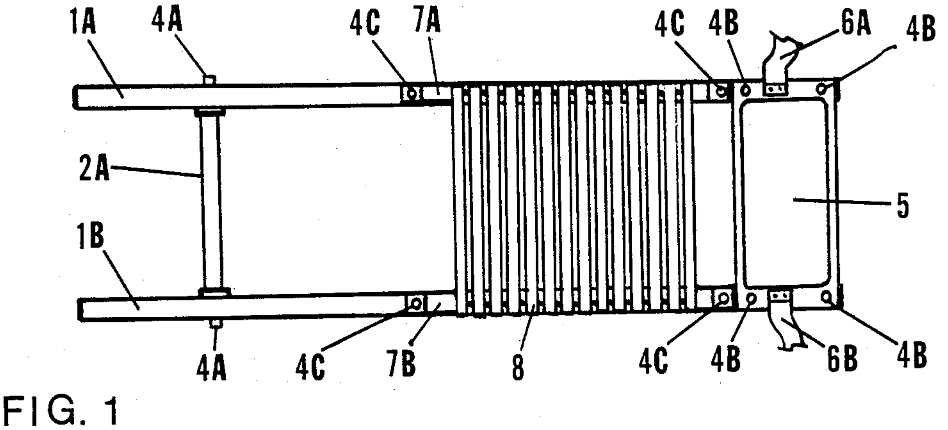
FIG. 1 shows a top view of the assembled apparatus.
Figure 2:
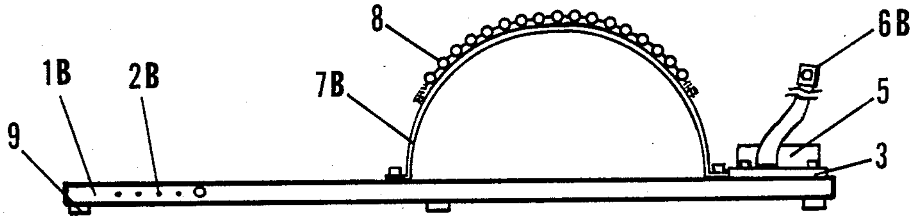
FIG. 2 shows a side view of the assembled apparatus, which is designed to be used on any flat surface at floor level.

With reference to FIGS. 1 and 2, there are only six basic parts to assemble; and only four different types. The two square tubular Base Rails 1A,1B are connected together by a Grip Rod 2 and the Kneeling Panel 3. Both of these connecting units are quickly bolted into place with the Knob Bolts 4A,4B, which are screwed into threaded inserts. There are also a series of hole locations 2B in the Base Rails 1A,1B for mounting the Grip Rod 2 at the correct location for the particular operator. The assembly includes the two Radius Supports 7A,7B. which are mounted by Knob Bolts 4C, and which support the Tubular Cover 8. There are also Rubber Feet 9 on the underside of the Base Rails 1A,1B to adapt the apparatus to either a smooth or carpeted floor.

Figure 5:
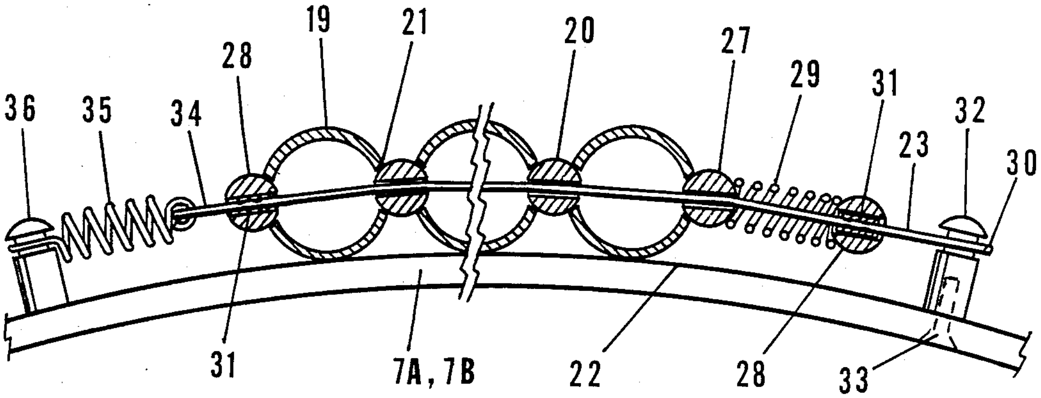
FIG. 5 shows a cross section of the Tubular Roll-Up Cover, thru the center line of the Separator Beads, when mounted over the Radius Supports; with the quick mounting and tensioning Terminator Springs.

Besides having strength and durability, the Tubular Cover 8 is quick to assemble, and equally quick to dissasemble, roll up, and store. These features are made possible by the unique construction of the Tubular Cover 8. Parallel metal or plastic Tubes 19 have round bevelled Bead Apertures 21 at each end, into which round Separator Beads 20 may nest, when they are alternately strung together with a strong Rentention Cord 23. The Retention Cord is, for example, flexible Nylon of about 0.080 inch diameter. FIG. 5 shows a lengthwise cross section of the Tubular Cover 8, thru the center line of the Beads 20 and the Cord 23; with the Cover 8 located over the Radius Support Surfaces 22.

Also shown in FIG. 5, are the two different Spring Terminations to the Retention Cord 23. Both spring terminations offer quick and easy assembly of the whole Tubular Cover 8 to the Radius Supports 7A,7B. The Mounting Studs 32,36 are identical, so it does not matter which end is which during the mounting of the Cover 8. The Tube Termination arrangement shown on the right hand side of FIG. 5 is made up of the End Bead 27, a Compression Spring 29, and a Termination Cover Bead 28; as well as the Cord Loop 30 and the cord loop Tubular Clamp 31. When the assembly is mounted, the Compression Spring 29 is under some compression to keep all of the Cover Tubes 19 tightly together, and the Separator Beads 20 snug in between the Tube Apertures 21. The Compression Spring 29 also takes up small variations of the center line length of the Cord 23 when the whole Tubular Cover 8 is rolled up.

The Tension Termination, on the left hand side of FIG. 5 is made up of a Termination Cover Bead 28, a Cord Loop 34, similar to the Loop 30 on the other end, and the Tension Spring 35, which is mounted on the Spring Mounting Stud 36. It is the function of the Tension Spring 35 to maintain a tight mounting of the cover for the life of the equipment; with whatever wear may occur on all of the cumulative Separator Bead Surfaces 20, or any long term stretch of the Nylon Cord 23. In Addition, the Spring takes up the length variations from the normal tolerences in the manufacture of all the series assembled parts.

Both type Cord Terminations (tension and compression) require a Metal Tube clamp 31 which is crimped over the ends of the Cord Loops 30,34, with indentations to grip the lubrous Nylon Cord 23. The cosmetic Cover Beads 28 and the Crimp Tubes 31 are held in place by friction and a strong adhesive such as epoxy.

Figure 6:
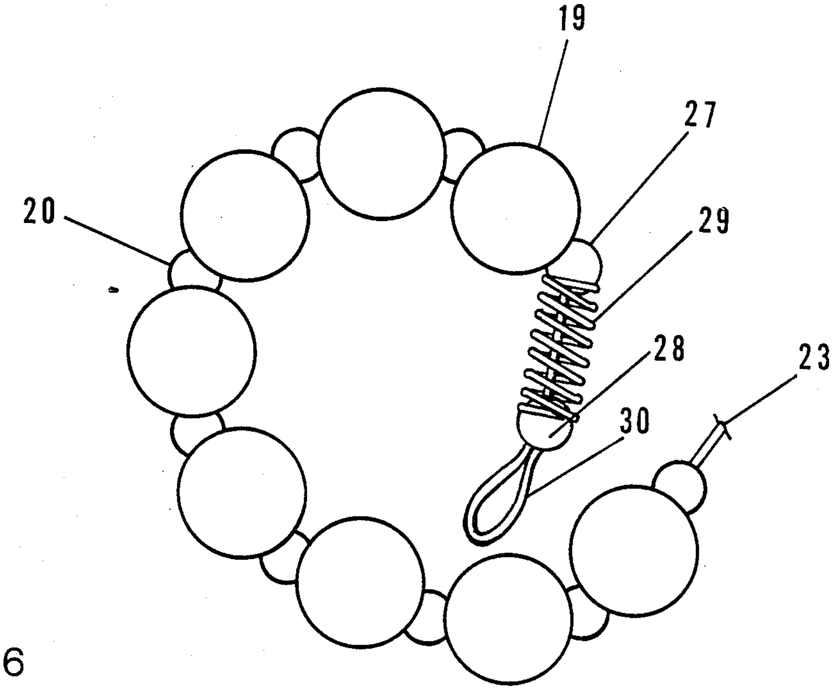
FIG. 6 shows a cross section of the Tubular Roll-Up Cover, as it would be rolled up for storage; with the Separator Beads acting as flexible ball joints.

FIG. 6 shows how easily the Tubular Cover 8 will roll-up, with the bead joints 20 allowing at least 45 degrees pivoting for each tube, with like termination parts being numbered as in the right side of FIG. 5.

Figure 7:
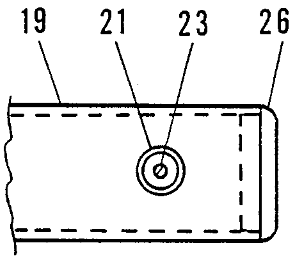
FIG. 7 shows the end detail of one of the individual plastic tubes which make up the Flexible Roll-Up Cover; with the end caps fused in the tube ends, and the bevelled holes for nesting the Separator Beads.

FIG. 7 shows a detail of a typical end of a hollow Cover Tube 19 with its lateral bevelled Aperture 21, and a cross section of the connecting Cord 23, with a solvent welded End Cap 26.

Figure 8:
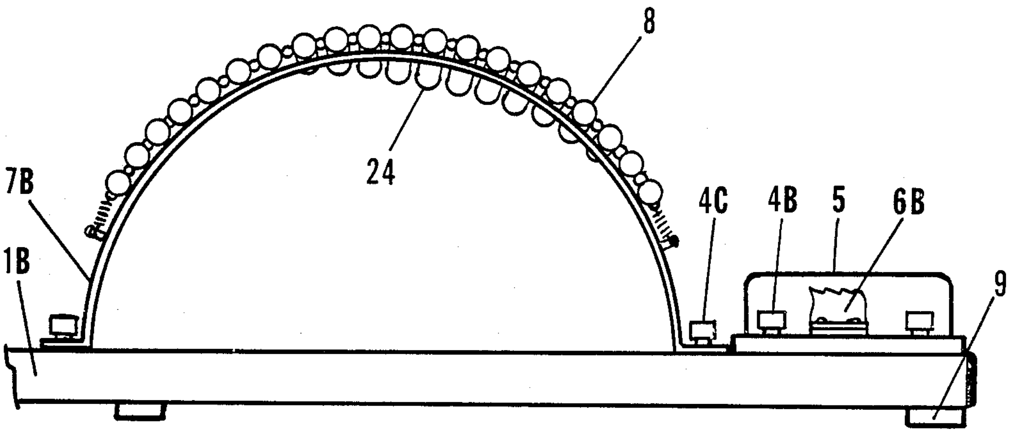
FIG. 8 shows a side view of the Tubular Cover, with individual Tube deflections, as may be caused by the shape of the operators abdomen.
Figure 9:
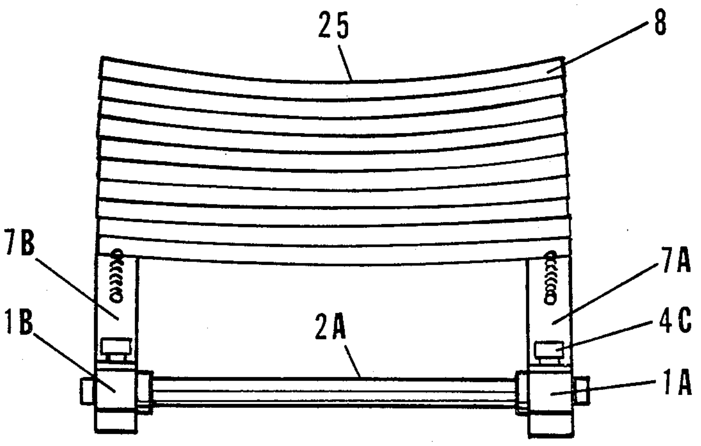
FIG. 9 shows the gradiated crosswise deflection of the separate tubes that make up the Tubular Cover, as they would appear from the kneeling end of the apparatus, when depressed by the shape of an operators abdomen.

FIGS. 8 and 9 show details of how the Tubular Cover 8 adapts its shape to the shape of the Operators Abdomen. A Particular Cover Tube 24 is shown with the most bend, to conform to the Operators shape. The tubes that are adjacent to the Tube 24 take their share of the load in proportion to the weight distribution; and they also provide a Crosswise Curved Surface 25, which affords additional comfort to the operator.

In summary, the new invention provides an economical and portable means for individuals to carry out self rehabilitation of curable back problems, which now cause an annual loss to the U.S. productivity of over 45 Billion dollars. Various medical sources agree that at least 75% of all back problems that are treated by Doctors and Chiropractors may be cured by manipulative means, such as the intermittant traction provided by the invention. The practicality and durability, as well as the uniqueness, of the new device has been shown in the forgoing description, and in the following appended claims.

I claim:

1. A method of self-actuated lombar traction, comprising the steps of:

applying and maintaining vertical support to the front of the knees of a patient to provide for the patient to kneel;

applying force to the back of the legs adjacent to the legs adjacent to the knees to maintain the knees in said kneeling condition;

applying vertical support to the front of the thighs, stomach, and lower chest of a patient to provide for the patient to position the upper chest, shoulders, head, and arms in a start position wherein the patient's back is substantially horizontal;

while maintaining said knees in said kneeling condition and while maintaining said vertical support to the front of the thighs, stomach, and lower chest, providing for the patient to use the hands to exert a pulling force to move the upper chest, shoulders, head, and arms in a downward direction so that the patient's back assumes an arcuate shape and the spinal column is caused to be in tension; and while maintaining said knees in said kneeling condition and while maintaining said vertical support to the front of the thighs, stomach, and lower chest, providing for the patient to move to return the upper chest, the shoulders, the head, and the arms to said start position.

2. Arcuately shaped torso support means for lombar traction apparatus, comprising:

a plurality of spaced apart tubes, the respective opposite ends of which have lateral openings;

a pair of cables respectively disposed adjacent opposite ends of said tubes and extending through said openings;

a plurality of separator beads respectively disposed between adjacent tubes and mounted on said cables and fitting into the lateral openings on adjacent tubes; and means connected with said tubes and with said cables for maintaining the tubes and separator beads in compressive engagement.

3. The method of self-actuated lombar traction, comprising the steps of:

applying and maintaining vertical support to the front of the knees of a patient to provide for the patient to kneel;

applying vertical support to the front of the thighs, stomach, and lower chest of a patient to provide for the patient to position the upper chest, shoulders, head, and arms in a start position wherein the patient's back is substantially horizontal;

while maintaining said vertical support to the front of the thighs, stomach, and lower chest, providing for the patient to move the upper chest, shoulders, head, and arms in a downward direction so that the patient's back assumes an arcuate shape and the weight of the head, shoulders, arms, and upper chest causes the spinal column to be in tension;

while maintaining said vertical support to the front of the thighs, stomach, and lower chest, providing for the patient to move to return the upper chest, the shoulders, the head, and the arms to said start position; and further providing means for the patient to utilize the arms to move, by a pulling force, the head, shoulders, and chest in said downward direction to increase said spinal column tension.

4. The construction of claim 3, further including;

retaining belt means connected to said kneeling means for use in surrounding the back of the legs of a patient kneeling on the kneeling means, to retain the legs in position.

5. Lombar traction apparatus comprising:

elongated base means;

kneeling means connected to said base means and spaced from said base means;

hand grip means connected to said base means;

arcuately shaped torso support means for supporting the torso of a patient, the opposite ends of the torso support means being connected to said base and extending upwardly from the base between said kneeling means and said hand grip means;

the torso support means including a plurality of space apart carriers extending laterally across said arcuately shaped torso support means; and said carriers comprising:

(a) a plurality of spaced apart tubes, the respective opposite ends of which have lateral openings;

(b) a pair of cables respectively disposed adjacent opposite ends of said tubes and extending through said openings;

(c) a plurality of separator beads respectively disposed between adjacent tubes and mounted on said cables and fitting into the openings on adjacent tubes; and (d) means connected with said tubes, with said cables, and with the torso support means to maintain the separated tubes and separator beads in compressive engagement and including, for each end of the respective cables, yielding connectors on the torso support means.

* * * * *